US010981958B2

(12) United States Patent
Vassilevski et al.

(10) Patent No.: US 10,981,958 B2
(45) Date of Patent: Apr. 20, 2021

(54) PEPTIDE MODULATOR OF PURINERGIC RECEPTORS

(71) Applicant: "FUTURE ANALGESICS" LIMITED, Moscow (RU)

(72) Inventors: Alexander Alexandrovich Vassilevski, Moscow (RU); Peter Borisovich Oparin, Moscow (RU); Yuliya Vladimirovna Korolkova, Moscow (RU); Irina Vladimirovna Mosharova, Moscow (RU); Ganna Anatolievna Savchenko, Kiev (UA); Yaroslav Anatolievich Boychuk, Kiev (UA); Oleg Alexandrovich Krishtal, Kiev (UA)

(73) Assignee: "FUTURE ANALGESICS" LIMITED, Moscow (RU)

( * ) Notice: Subject to any disclaimer, the term of this patent is extended or adjusted under 35 U.S.C. 154(b) by 72 days.

(21) Appl. No.: 16/466,885

(22) PCT Filed: May 31, 2017

(86) PCT No.: PCT/RU2017/000279

§ 371 (c)(1),
(2) Date: Jun. 5, 2019

(87) PCT Pub. No.: WO2018/106142

PCT Pub. Date: Jun. 14, 2018

(65) Prior Publication Data

US 2020/0207815 A1 Jul. 2, 2020

(30) Foreign Application Priority Data

Dec. 6, 2016 (RU) ................................ 2016147736

(51) Int. Cl.
*C07K 14/435* (2006.01)
*A61K 38/16* (2006.01)
*A61K 38/00* (2006.01)

(52) U.S. Cl.
CPC ............ *C07K 14/435* (2013.01); *A61K 38/00* (2013.01)

(58) Field of Classification Search
None
See application file for complete search history.

(56) References Cited

U.S. PATENT DOCUMENTS 6,881,725 B2 4/2005 Yerxa et al.
7,491,821 B2 2/2009 Brotherton-Pleiss et al.
7,531,547 B2 5/2009 Dillon et al.
7,589,090 B2 9/2009 Dillon et al.
7,595,405 B2 9/2009 Dillon et al.

FOREIGN PATENT DOCUMENTS

RU 2 422 459 6/2011
RU 2 571 942 12/2015

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
International Search Report for PCT/RU2017/000279, dated Oct. 12, 2017, 2 pages.
Grishin et al., "Novel peptide from spider venom inhibits P2X3 receptors and inflammatory pain", ANNALS of Neurology, 2010. vol. 67, No. 5, pp. 680-683.
Kabanova et al., "Modulation of P2X3 receptors by spider toxins", Biochimica et Biophysica Acta, 2012, pp. 2868-2875, vol. 1818.
Brotherton-Pleiss et al., "Discovery and optimization of RO-85, a novel drug-like, potent, and selective $P2X_3$ receptor antagonist", Bioorganic & Medicinal Chemistry Letters, 2010, pp. 1031-1036, vol. 20.
Carter et al., "Identification and SAR of novel diaminopyrimidines. Part 1: The discovery of RO-4, a dual $P2X_3/P2X_{2/3}$ antagonist for the treatment of pain", Bioorganic & Medicinal Chemistry Letters, 2009, pp. 1628-1631, vol. 19.
Donnelly-Roberts et al., "Painful Purinergic Receptors", The Journal of Pharmacology and Experimental Therapeutics, vol. 324, No. 2, pp. 409-415.
Virginio et al., "Trinitrophenyl-Substituted Nucleotides Are Potent Antagonists Selective for $P2X_1$, $P2X_3$, and Heteromeric $P2X_{2/3}$ Receptors", Molecular Pharmacology, 1998, vol. 53, pp. 969-976.

(Continued)

*Primary Examiner* — Christine J Saoud
*Assistant Examiner* — Jon M Lockard
(74) *Attorney, Agent, or Firm* — Nixon & Vanderhye P.C.

(57) ABSTRACT

The invention refers to medicine and pharmacology, namely, to biologically active peptides, which modulate purinergic signaling. For that, the peptide with the following amino acid sequence is proposed:

$Gly^{1}$-$Tyr^{2}$-$Cys^{3}$-$Ala^{4}$-$Thr^{5}$-$Lys^{6}$-$Gly^{7}$-$Ile^{8}$-$Lys^{9}$-$Cys^{10}$-$Asn^{11}$-$Asp^{12}$-$Ile^{13}$-$His^{14}$-$Cys^{15}$-$Cys^{16}$-$Ser^{17}$-$Gly^{18}$-$Leu^{19}$-$Lys^{20}$-$Cys^{21}$-$Asp^{22}$-$Ser^{23}$-$Lys^{24}$-$Arg^{25}$-$Lys^{26}$-$Val^{27}$-$Cys^{28}$-$Val^{29}$-$Lys^{30}$-$Gly^{31}$, or a sequence with at least 90% homology hereto.

Peptides in the invention can be used for prevention and treatment of diseases mediated by purinergic receptors. The peptides can be used for development of new drugs on their basis, for example, analgesics, as well for investigation of mechanisms of pain occurrence, for identification and testing of new modulators of P2X3 receptors. The peptides in the invention can be produced using chemical synthesis or biotechnologically using the nucleotide sequence of the corresponding gene.

2 Claims, 1 Drawing Sheet

Specification includes a Sequence Listing.

(56) References Cited

OTHER PUBLICATIONS

Ford et al., "The $P2X_3$ Antagonist $P^1$, $P^5$-Di[inosine-5'] Pentaphosphate Binds to the Desensitized State of the Receptor in Rat Dorsal Root Ganglion Neurons", The Journal of Pharmacology and Experimental Therapeutics, 2005, vol. 315, pp. 405-413.

Altschul et al., "Basic Local Alignment Search Tool", J. Mod. Biol., 1990, vol. 215, pp. 403-410.

Altschul et al., "Gapped BLAST and PSI-BLAST: a new generation of protein database search programs", Nucleic Acids Research, 1997, vo. 25. No. 17, pp. 3389-3402.

Hausmann et al., "The Suramin Analog 4,4',4",4"'-(Carbonylbis(imino-5,1,3-benzenetriylbis (carbonylimino)))tetra-kis-benzenesulfonic Acid (NF110) Potently Blocks $P2X_3$ Receptors: Subtype Selectivity is Determined by Location of Sulfonic Acid Groups", Molecular Pharmacology, vol. 69, No. 6, pp. 2058-2067.

Jahangir et al., "Identification and SAR of novel diaminopyrimidines. Part 2: The discovery of RO-51, a potent and selective, dual $P2X_3/P2X_{2/3}$ antagonist for the treatment of pain", Bioorganic & Medicinal Chemistry Letters, vol. 19, 2009, pp. 1632-1635.

Burgard et al., "P2X Receptor—Mediated Ionic Currents in Dorsal Root Ganglion Neurons", The American Physiological Society, 1999, pp. 1590-1598.

Jung et al., "Structure-Activity Relationship Studies of Spinorphin as a Potent and Selective Human $P2X_3$ Receptor Antagonist", Journal of Med. Chem., 2007,vol. 50, pp. 4543-4547.

Jarvis et al., "A-317491, a novel potent and selective nonnucleotide antagonist of $P2X_3$ and $P2X_{2/3}$ receptors, reduces chronic inflammatory and neuropathic pain in the rat", PNAS, Dec. 24, 2002, vol. 99, No. 26, pp. 17179-17184.

Wirkner et al., "$P2X_3$ Receptor Involvement in Pain States", Mol. Neurobiol, 2007, vol. 36, pp. 168-183.

* cited by examiner

```
                         SEQUENCE LISTING

<160> NUMBER OF SEQ ID NOS: 1

<210> SEQ ID NO 1
<211> LENGTH: 31
<212> TYPE: PRT
<213> ORGANISM: Artificial sequence
<220> FEATURE:
<223> OTHER INFORMATION: Artificial peptide modulates the activity of
      purinergic P2X3 receptors

<400> SEQUENCE: 1

Gly Tyr Cys Ala Thr Lys Gly Ile Lys Cys Asn Asp Ile His Cys Cys
1               5                   10                  15

Ser Gly Leu Lys Cys Asp Ser Lys Arg Lys Val Cys Val Lys Gly
            20                  25                  30
```

PEPTIDE MODULATOR OF PURINERGIC RECEPTORS

This application is the U.S. national phase of International Application No. PCT/RU2017/000279 filed 31 May 2017, which designated the U.S. and claims priority to RU Patent Application No. 2016147736 filed 6 Dec. 2016, the entire contents of each of which are hereby incorporated by reference.

TECHNICAL FIELD

The invention refers to medicine and pharmacology, namely, to biologically active peptides that modulate purinergic signaling and can be used for the prevention and treatment of diseases, in which purinergic receptors represent a pharmacological target.

BACKGROUND OF THE INVENTION

Pain research and treatment are significant aspects that should be considered to improve the quality of life of patients. Pain treatment is mainly based on administration of anti-inflammatory drugs such as non-steroidal anti-inflammatory drugs (NSAIDs) or steroid (corticosteroid) drugs, antidepressants and anticonvulsants, as well strong or weak opiates. NSAIDs form the most commonly used class of therapeutic products due to their high efficacy and since they target both the inflammatory process and pain itself. They are used to treat all types of inflammatory pain including acute and chronic pain. Although NSAIDs are very effective agents, they remain a serious source of adverse effects limiting applicability in numerous clinical situations. Despite a large number of therapeutic agents, many types of pain remain weakly sensitive to known analgesics. Therefore, development of new analgesic agents with new modes of action is an important challenge.

Ionotropic purinergic receptors (P2X) are ligand-gated ion channels, which are activated by their natural agonist adenosine triphosphate (ATP) applied extracellularly. These receptors are found in various organs and tissues, and they have a specific physiological function in the nervous system [Surprenant A., North R. A. Signaling at purinergic P2X receptors//Annu. Rev. Physiol., 2009, Vol. 71, p. 333-359]. P2X are expressed in sensory neurons, and ATP released from damaged and inflamed tissues, activates the receptors and initiates pain signals. It is assumed that purinergic signaling plays an important role in pain conditions related to injuries, tumors, inflammation, migraine and respiratory diseases. Humans have seven known isoforms of P2X receptors among which isoforms P2X2, P2X3, P2X4 and P2X7 are assumed to participate in pain perception [Donnelly-Roberts D. et al. Painful purinergic receptors//J. Pharmacol. Exp. Ther., 2008, Vol. 324, p. 409-415]. Among the seven isoforms of purinergic receptors, P2X3 is acknowledged to be an important and well-known “participant” of pain conditions [Wirkner K. et al. P2X3 receptor involvement in pain states//Mol. Neurobiol., 2007, Vol. 36, p. 165-183].

Selective modulators of purinergic receptor function, which are able to modify the activity of only particular isoforms, are key to drug development for the treatment of diseases, in which these receptors are involved. They are also necessary for the investigation of purinergic receptor functions. In case of P2X3 receptors, antagonists (inhibitors) have the greatest pharmacological potential, as it is exactly the decrease of receptor activity that is required for the therapy of several pain syndromes.

Nowadays, numerous low-molecular-mass antagonists of P2X3 receptors are known, for example: 2',3'-O-(2,4,6-trinitrophenyl)-ATP [Virginio C. et al. Trinitrophenyl-substituted nucleotides are potent antagonists selective for P2X1, P2X3, and heteromeric P2X2/3 receptors//Mol. Pharmacol., 1998, Vol. 53, p. 969-973], other derivates of mono- and dinucleotides and [Ford K. K. et al. The P2X3 antagonist P1, P5-di[inosine-5'] pentaphosphate binds to the desensitized state of the receptor in rat dorsal root ganglion neurons//J. Pharmacol. Exp. Ther., 2005, Vol. 315, p. 405-413; U.S. Pat. No. 6,881,725], suramin analogues [Hausmann R. et al. The suramin analog 4,4',4",4'"-(carbonylbis(imino-5, 1,3-benzenetriylbis (carbonylimino)))tetra-kis-benzene-sulfonic acid (NF110) potently blocks P2X3 receptors: subtype selectivity is determined by location of sulfonic acid groups//Mol. Pharmacol., 2006, Vol. 69, p. 2058-2067], A-317491 [Jarvis M. F. et al. A-317491, a novel potent and selective non-nucleotide antagonist of P2X3 and P2X2/3 receptors, reduces chronic inflammatory and neuropathic pain in the rat//Proc. Natl. Acad. Sci. U.S.A., 2002, Vol. 99, p. 17179-17184], diaminopyrimidine derivatives [Carter D. S. et al. Identification and SAR of novel diaminopyrimidines. Part 1: The discovery of RO-4, a dual P2X3/P2X2/3 antagonist for the treatment of pain//Bioorg. Med. Chem. Lett. 2009, Vol. 19, p. 1628-1631; Jahangir A. et al. Identification and SAR of novel diaminopyrimidines. Part 2: The discovery of RO-51, a potent and selective, dual P2X3/P2X2/3 antagonist for the treatment of pain//Bioorg. Med. Chem. Lett., 2009, Vol. 19, p. 1632-1635; U.S. Pat. Nos. 7,589,090; 7,531,547], tetrazole and arylamide derivatives [U.S. Pat. No. 7,595,405], as well as piperazine and phenyl thienopyrazole derivatives [Brotherton-Pleiss C. E. Discovery and optimization of RO-85, a novel drug-like, potent, and selective P2X3 receptor antagonist//Bioorg. Med. Chem. Lett., 2010, Vol. 20, p. 1031-1036; U.S. Pat. No. 7,491,821].

Among inhibitors of P2X3 receptors, substances of protein nature are known: spinorphin, a fragment of hemoglobin β-chain affecting also other targets [Jung K. Y. et al. Structure-activity relationship studies of spinorphin as a potent and selective human P2X3 receptor antagonist//J. Med. Chem., 2007, Vol. 50, p. 4543-4547], and two components of the spider *Alopecosa marikovskyi* venom, namely, purotoxin-1 (PT1) [Grishin E. V. et al. Novel peptide from spider venom inhibits P2X3 receptors and inflammatory pain//Ann. Neurol., 2010, Vol. 67, p. 680-683; RU2422459] and purotoxin-2 (PT2) [Kabanova N. V. et al. Modulation of P2X3 receptors by spider toxins//Biochim. Biophys. Acta, 2012, Vol. 1818, p. 2868-2875]. PT1 is the closest analogue of the declared compounds. This peptide consists of 35 amino acid residues and inhibits selectively the activity of P2X3 receptors due to stabilization of their desensitized state. Recombinant PT1 can be produced in a bacterial expression system [Grishin E. V. et al. Novel peptide from spider venom inhibits P2X3 receptors and inflammatory pain//Ann. Neurol., 2010, Vol. 67, p. 680-683; RU2422459; RU257194].

Despite rather numerous known compounds, which can inhibit P2X3 receptors, no drug has currently been approved for the use in clinical practice acting as a P2X3 modulator. Meanwhile, the search for new drugs relieving pain of any origin effectively and safely is a pressing challenge for modern medicine. The development and implementation of effective and selective modulators of P2X3 receptors can be one of the approaches for solving the task.

DISCLOSURE OF THE INVENTION

The goal of the invention is the development and production of new antagonists of purinergic P2X3 receptors prospective for use in clinical practice.

The technical result of the invention is the derivation of new effective peptides modulating the activity of purinergic P2X3 receptors and being selective with respect to P2X3, highly stable and prospective for use in treatment of mammalian diseases or conditions, in which the pharmacological target is represented by purinergic P2X3 receptors, and in particular, in pain states of various etiology.

Moreover, an additional technical result shows that the peptides are characterized by simple structure in comparison with the prototype, can be easily produced in a bacterial expression system, and are prospective for the development of drugs on their basis.

The specified technical result is achieved by the development and production of a peptide modulating the activity of purinergic P2X3 receptors with the following amino acid sequence:

SEQ ID NO: 1

$Gly^1$-$Tyr^2$-$Cys^3$-$Ala^4$-$Thr^5$-$Lys^6$-$Gly^7$-$Ile^8$-$Lys^9$-$Cys^{10}$-$Asn^{11}$-$Asp^{12}$-$Ile^{13}$-$His^{14}$-$Cys^{15}$-$Cys^{16}$-$Ser^{17}$-$Gly^{18}$-$Leu^{19}$-$Lys^{20}$-$Cys^{21}$-$Asp^{22}$-$Ser^{23}$-$Lys^{24}$-$Arg^{25}$-$Lys^{26}$-$Val^{27}$-$Cys^{28}$-$Val^{29}$-$Lys^{30}$-$Gly^{31}$ or having a sequence of at least 90% homology hereto.

In some variants of the invention implementation, the peptide modulating the activity of purinergic P2X3 receptors has the following amino acid sequence:

SEQ ID NO: 1

$Gly^1$-$Tyr^2$-$Cys^3$-$Ala^4$-$Thr^5$-$Lys^6$-$Gly^7$-$Ile^8$-$Lys^9$-$Cys^{10}$-$Asn^{11}$-$Asp^{12}$-$Ile^{13}$-$His^{14}$-$Cys^{15}$-$Cys^{16}$-$Ser^{17}$-$Gly^{18}$-$Leu^{19}$-$Lys^{20}$-$Cys^{21}$-$Asp^{22}$-$Ser^{23}$-$Lys^{24}$-$Arg^{25}$-$Lys^{26}$-$Val^{27}$-$Cys^{28}$-$Val^{29}$-$Lys^{30}$-$Gly^{31}$ or a sequence of at least 95% homology hereto.

In another variant of the invention implementation, the peptide modulating the activity of purinergic P2X3 receptors has the following amino acid sequence:

SEQ ID NO: 1

$Gly^1$-$Tyr^2$-$Cys^3$-$Ala^4$-$Thr^5$-$Lys^6$-$Gly^7$-$Ile^8$-$Lys^9$-$Cys^{10}$-$Asn^{11}$-$Asp^{12}$-$Ile^{13}$-$His^{14}$-$Cys^{15}$-$Cys^{16}$-$Ser^{17}$-$Gly^{18}$-$Leu^{19}$-$Lys^{20}$-$Cys^{21}$-$Asp^{22}$-$Ser^{23}$-$Lys^{24}$-$Arg^{25}$-$Lys^{26}$-$Val^{27}$-$Cys^{28}$-$Val^{29}$-$Lys^{30}$-$Gly^{31}$.

The present invention refers also to the use of the peptides being invented, as modulators of purinergic P2X3 receptors.

The present invention refers also to the use of the peptides being invented, as antagonists of purinergic P2X3 receptors.

The present invention refers also to the use of the peptides being invented for creation of a pharmaceutical composition for the treatment and/or prevention of conditions associated with purinergic P2X3 receptors, for example, during therapy of pain of various etiology and/or pain symptoms, in particular, inflammation pain, postoperative pain, visceral pain, dental pain, premenstrual pain, pain induced by burns, migraine or cluster headache, pain in nerve damage, neuritis, neuralgias, pain in oncological diseases or pain related to the irritated bowel syndrome.

The invention includes also production of the peptides being invented. The peptides can be derived by genetic engineering or chemical synthesis.

Definition and Terms

As used in the present document, the term "peptide PT6" refers to the peptide with the following amino acid sequence:

SEQ ID NO: 1

$Gly^1$-$Tyr^2$-$Cys^3$-$Ala^4$-$Thr^5$-$Lys^6$-$Gly^7$-$Ile^8$-$Lys^9$-$Cys^{10}$-$Asn^{11}$-$Asp^{12}$-$Ile^{13}$-$His^{14}$-$Cys^{15}$-$Cys^{16}$-$Ser^{17}$-$Gly^{18}$-$Leu^{19}$-$Lys^{20}$-$Cys^{21}$-$Asp^{22}$-$Ser^{23}$-$Lys^{24}$-$Arg^{25}$-$Lys^{26}$-$Val^{27}$-$Cys^{28}$-$Val^{29}$-$Lys^{30}$-$Gly^{31}$.

The term "to modulate" in the present document means to change the functional characteristics of purinergic P2X receptors, in particular, to inhibit, block, reduce or prevent physiological effects induced by agonist-receptor binding (including the endogenous agonist), in particular, P2X3 receptors.

The term "modulator" in the present document means the substance which can modulate, i.e. change the functional characteristics of purinergic P2X receptors, in particular, to inhibit, block, reduce or prevent physiological effects induced by agonist-receptor binding (including the endogenous agonist), in particular, P2X3 receptors.

"Antagonist" (receptor antagonist) in biochemistry and pharmacology refers to a subtype of ligands to cell receptors. A ligand with the properties of a receptor antagonist is a ligand, which inhibits, blocks, reduces or prevents physiological effects induced by agonist-receptor binding (including the endogenous agonist).

An antagonist is called "selective" if it inhibits certain receptor or subtype of receptors. The degree of selectivity can vary.

The term "homologous" (or "homology") is the synonym of "identity" in the present invention and means the similarity of peptide sequences. In the present invention, the degree of sequence identity means the similarity between amino acid sequences and is determined by comparison of two optimally aligned sequences in the window of comparison, and some part of the amino acid sequence in the window of comparison can contain insertions or deletions (i.e. gaps) in comparison with the control sequence (not containing insertions or deletions) for an optimal alignment of two sequences. The degree of identity can be calculated by determination of the number of positions in which identical amino acid residues are found in both sequences, obtaining the number of coinciding positions, dividing the number of coinciding positions by the total number of positions in the window of comparison and multiplying the result by 100, providing the percentage of sequence identity. Specialists can be aware that numerous established algorithms exist for alignment of two sequences. Algorithms BLAST and BLAST 2.0 are examples of algorithms being suitable for the determination of sequence identity [Altschul S. F. et al. Basic local alignment search tool//J. Mol. Biol., 1990, Vol. 215, p. 403-410; Altschul S. F. et al. Gapped BLAST and PSI-BLAST: a new generation of protein database search programs//Nucleic Acids Res., 1997, Vol. 25, p. 3389-3402].

Homologous peptides have identical or similar amino acid sequences. In the context of the present invention, similar residues represent "conservative substitutions" or "allowed point mutations" of corresponding amino acid residues in the control sequence. Conservative substitutions in the control sequence are such replacements, which are similar physically or functionally to the corresponding control residues, for example, have similar size, form, electric charge, chemical properties including the ability to form covalent or hydrogen bonds, etc. It is evident for a specialist in the field that all homologous peptides being invented are able to modulate efficiently the activity of P2X3 receptors.

In the context used herein, the term "treatment" means a method for getting favorable or desirable clinical results. In accordance with the aims of the present invention, favorable or desirable clinical results include but are not limited to one or several aspects stated below: reduction of any manifestation, in particular, of pain of various etiology including pain intensity, relief of any or several pain symptoms such as reduction of pain perception and/or sensation, temporary pain relief and/or retardation.

Term "reduction of pain manifestation" means any methods for pain relief (which can include reduction of the need in drugs and/or reduction of the amount of other drugs used commonly in the condition), reduction of pain duration, intensity and/or occurrence (for example, including time to occurrence of pain of various etiology).

Term "reduction of pain intensity" of various etiology means reduction or improvement of one or several pain symptoms compared to pain persisting without administration of the modulator of P2X3 receptors. Term "reduction of intensity" means also the reduction of symptom duration.

Term "temporary relief" of pain of various etiology of one or several pain symptoms means the reduction of a manifestation of one or several adverse clinical pain effects in one or several subjects treated with the modulator of P2X3 receptors in accordance with the present invention.

In the context used herein, term "retardation" of pain of various etiology means suppression, prevention, delay, stabilization and/or delay of pain progression. Such retardation can vary in time depending on clinical history and/or treated subject. As it should be evident for a specialist in the field, a considerable or significant retardation may include pain prevention expressed so that pain does not occur any longer. The method of symptom "retardation" is the method, which reduces the symptom manifestation probability during a period of time and/or reduces the symptom manifestation in the period of time compared to the situation when the method is not applied. Such comparisons are usually based on clinical studies involving a number of subjects sufficient to get a significant result.

(A) Separation of products of fusion protein hydrolysis with enteropeptidase on a Jupiter $C_4$ column (10×250 mm). Fraction corresponding to PT6 is indicated (*).

(B) Second step chromatography of isolated PT6 on a Vydac C18 column (4.6×250 mm).

Figure 2:
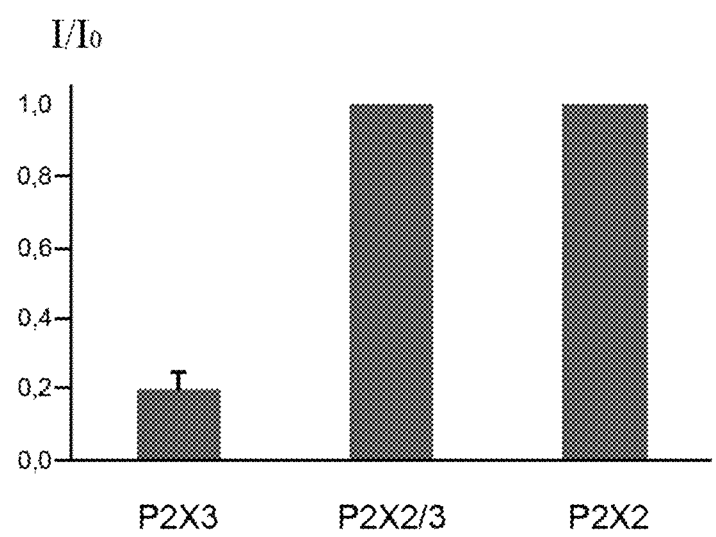

FIG. 2. Effect of PT6 peptide on the currents mediated by P2X receptors in the neuronal culture of rat dorsal root ganglia. The histogram shows a relative value of residual currents (I) mediated by homomeric P2X3, heteromeric P2X2/3 and homomeric P2X2 receptors, with PT6 applied in concentration of 50 nM compared to the control in the absence of PT6 ($I_0$).

DETAILED DISCLOSURE OF THE INVENTION

The assigned task of the invention is solved by the production of peptides of the invention modulating the activity of purinergic P2X3 receptors. Thus, the sequence of peptide PT6, in particular, is determined by the analysis of mRNA from venom glands of araneomorph spiders, namely, the specified sequence of peptide PT6 is provided by the analysis of a cDNA library of the spider *Thomisus onustus* glands. Peptides of the invention, in particular peptide PT6, are substances of polypeptide (protein) nature and can be produced by chemical synthesis or genetic engineering methods.

It has been suddenly discovered that the declared peptides can inhibit purinergic P2X3 receptors. So peptide PT6, in particular, in concentration of 50 nM induces 80% inhibition of the currents mediated by P2X3 receptors in rat sensory neurons. PT6 is a selective antagonist of purinergic P2X3 receptors.

Peptide-based products of the invention are prospective for the therapy of pain of various etiology, in particular, inflammatory pain, postoperative pain, visceral pain, dental pain, premenstrual pain, pain induced by burns, migraine or cluster headache, pain in nerve damage, neuritis, neuralgia, pain in oncological diseases or pain associated with the irritated bowel syndrome. Peptides in the invention can be used, in particular, for reduction of pain manifestation, decrease of pain intensity, for temporary pain relief or retardation of pain of various etiology.

Moreover, peptide PT6 is characterized by an extremely stable structure (it contains the so-called "cystine knot" motif), can be easily produced in a bacterial expression system and differs by structural simplicity compared to the prototype (peptide PT1, RU2422459): it is shorter by four residues and contains one disulfide bond less than peptide PT1; PT6 contains six cysteine residues forming three intramolecular disulfide bonds. This serves as evidence in favor of the assumption of a high potential of PT6 in terms of drug development.

IMPLEMENTATION OF THE INVENTION

The possibility to unequivocally achieve the technical result during the implementation of the invention is confirmed by reliable data provided in examples containing experimental facts. It should be understood that these and all examples provided are not limiting and are presented only to illustrate the present invention.

Production of Recombinant Peptide PT6

Amino acid sequence of peptide PT6 is reverse-translated to a corresponding nucleotide sequence with regards to the frequency of codon usage in *Escherichia coli*. Several oligonucleotide fragments of up to 50 nucleotides in length are synthesized overlapping the full sequence of PT6 gene, and the terminal fragments contain restriction sites for cloning to plasmid pET-32b (Novagen, USA):

```
f1,
5'-TTTCGGTACCGGCTATTGCGCGACCAAAGGCATTAAATGCAA-3',

f2,
5'-CGATATTCATTGCTGCAGCGGCCTGAAATGCGATAGCAAACGCAAAG
TGT-3',

r1,
5'-CTGCAGCAATGAATATCGTTGCATTTAATGCCTTTG-3',

r2,
5'-ATACGGATCCTTAGCCTTTCACGCACACTTTGCGTTTGCTAT-3'.
```

The synthesis of the full-sized gene sequence encoding peptide PT6 is performed using the methods of DNA ligation and PCR. For that, 3'-termini of the fragments are phosphorylated using polynucleotide kinase (Promega, USA) at 37° C. for 30 min; ligation is performed with T4

DNA ligase (Promega) for 18 h at 16° C. PCR is performed using a standard procedure on a PTC-200 Thermal cycler (MJ Research, USA). The reaction mixture contains: PCR buffer (50 mM KCl, 1.5 mM $MgCl_2$, 0.1% Tween 20, 50 mM Tris-HCl, pH 8.6), a mixture of four deoxynucleotides (Promega), primer (terminal) oligonucleotides (5'-GGCTATTGCGCGACCA-3' and 5'-TTAGCCTTTCACGCACAC-3), matrix DNA (ligase mixture) and Taq-polymerase. PCR conditions: denaturation (96° C.), 20 sec; hybridization (50° C.), 20 sec; elongation (72° C.), 30 sec; 25 cycles. Then the PCR product and plasmid pET-32b are restricted in buffer MultiCore, which is optimal for the activity of enzymes BamHI and KpnI (Promega). As the control, the plasmid is restricted with each of the enzymes separately, the result is assessed by the change of the vector mobility in agarose gel electrophoresis. The restricted DNA fragments and vector are purified with agarose gel electrophoresis and further DNA isolation from the gel using the Wizard SV Gel and PCR Clean-Up System kit (Promega) in accordance with the manufacturer's protocol. The synthetic PT6 gene and pET-32b vector are ligated with each other using T4 DNA ligase. As a result, the plasmid encoding protein chimera of thioredoxin with PT6 under the control of T7 promoter is produced.

The obtained plasmids are used for transformation of *E. coli* XL1 Blue cells using a Cellject electroporation system (Eurogentec, Belgium). The electric impulse parameters are set in accordance with the recommendations of the producer of the electroporation unit. Cell suspension is placed on a Petri dish containing solid LB medium (1% bacto tryptone, 0.5% yeast extract, 1% NaCl, 1.5% agar, 10 mM Tris-HCl, pH 7.6) with addition of ampicillin (70 μg/ml) as a selective factor. The dishes are incubated at 37° C. for 18 h. Colonies of *E. coli* XL1 Blue, derived on the selective medium after transformation are seeded on a new Petri dish with solid LB medium containing ampicillin (70 μg/ml). The dishes are incubated for 18 h at 37° C. PCR is performed with primers specific to the concerned sequence (5'-GGCTATTGCGCGACCA-3' and 5'-TTAGCCTTTCACGCACAC-3), the total nucleic acid from the obtained cell mass is used as the matrix. The selected transformants are used for the production of an overnight liquid culture in 5 ml of liquid LB medium with ampicillin (70 μg/ml), the suspension is incubated for 18 h at 37° C. The procedure of the preparative isolation of plasmid DNA is performed using the Wizard Plus SV Minipreps DNA Purification System kit (Promega) in accordance with the manufacturer's protocol.

The accuracy of the assembly and ligation are checked by Sanger sequencing using a Model 373 DNA Sequencer (Applied Biosystems, USA) and the following reagents: ABI PRISM BigDye Terminator Cycle Sequencing Ready reaction kit, AmpliTaq DNA polymerase, FS (Perkin Elmer, USA) and pET-HindSeq primer (5'-CTTCCTTTCGGGCTTTG-3') in accordance with the recommendations of the manufacturers.

Fusion protein is produced using controlled expression of the corresponding gene in *E. coli* BL21(DE3) cells. Overnight bacterial culture transformed with the expression vector pET-32b containing the PT6 gene insertion, is diluted 200-fold using LB medium with ampicillin (100 μg/ml). The cells are incubated at 37° C. on a shaker (200 rpm) up to reaching optical density of $OD_{620}$=0.6, after which the inducer (isopropyl-β-D-1-thiogalactopyranoside, IPTGTI⁻; 0.2 mM) is added to the culture, which is then incubated at room temperature for 18 h.

Cells are collected by centrifugation (10 min, 4500 rpm) and resuspended in 25 ml of the starting buffer for affinity chromatography (see below) with addition of 1% Triton X-100. The cells are disrupted using a CPX 750 Ultrasonic Homogenizer (Cole-Parmer Instruments, USA). The fusion protein is isolated with affinity chromatography. The cell lysate is applied in the starting buffer (50 mM Tris-HCl, pH 8, 300 mM NaCl) to a 3-ml column with the TALON Superflow Metal Affinity Resin (Clontech, USA) at a flow rate of 1 ml/min. Buffer containing 50 mM Tris-HCl, pH 8, 300 mM NaCl, 150 mM imidazole is used for the elution of the target protein. It is detected by effluent absorbance at 280 nm. Isolation and purification of the fusion protein are controlled by polyacrylamide gel electrophoresis of aliquots of the obtained fractions.

Figure 1:
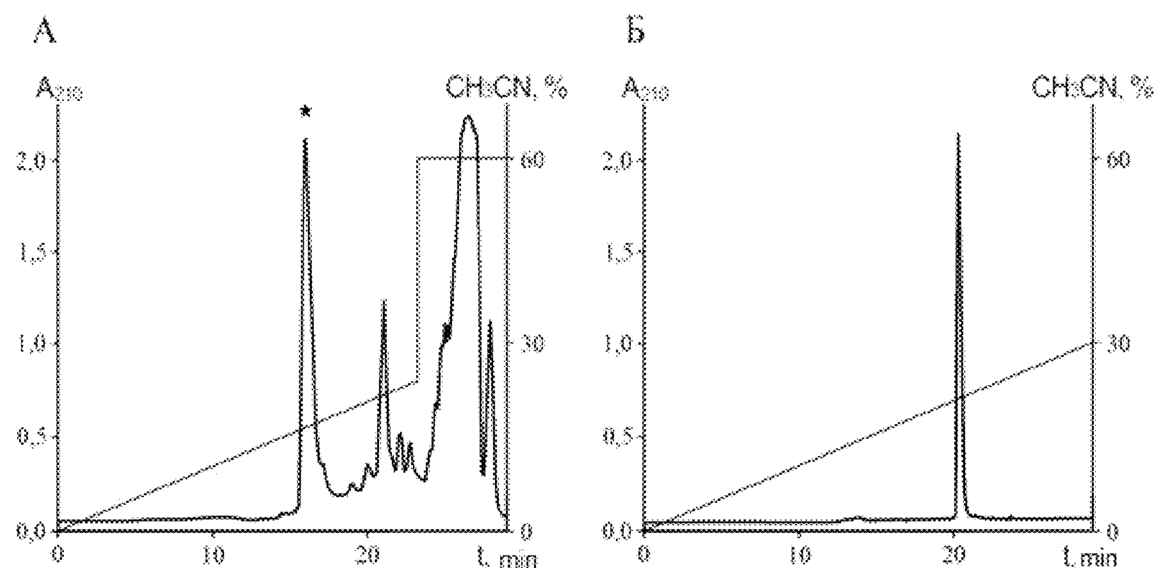
FIG. 1. Production of recombinant peptide PT6.

The resulting protein is desalted on a Jupiter $C_4$ column (10×250 mm, 300 Å, 10 μm; Phenomenex, USA). Elution is performed by a step-wise change of acetonitrile concentration (0-70%) in 0.1% trifluoroacetic acid (TFA) at a flow rate of 2 ml/min. The protein is dried on a vacuum concentrator, dissolved in 50 mM Tris-HCl, pH 8, to a final concentration of ~1 mg/ml. A solution of human enteropeptidase catalytic subunit is added to the protein solution at 1 unit per 1 mg of protein, the hydrolysis is performed at room temperature for 18 h. Hydrolysis products of the fusion protein are separated on a Jupiter $C_4$ column (10×250 mm) in a linear gradient of acetonitrile concentration (0-24% for 24 min, 23-60% for 1 min) in 0.1% TFA at a flow rate of 2 ml/min. Detection is performed by effluent absorbance at 210 nm (FIG. 1A). The purity of the resulting PT6 product is confirmed by a second step chromatography on a Vydac 218TP54 C18 column (4.6×250 mm, 300 Å, 5 μm; Separations Group, USA) in a linear gradient of acetonitrile concentration (0-30% for 30 min) in 0.1% TFA at a flow rate of 1 ml/min (FIG. 1B). As a result, the yield of recombinant PT6 is 5 mg per 1 liter of bacterial culture. The recombinant peptide structure is confirmed using mass spectrometry and N-terminal sequencing.

It is evident for a specialist in the field that all peptides being invented and having a sequence, which is homologous to the sequence of peptide PT6, at least by 90%, or in particular by 95%, can be obtained using an analogous method.

Investigation of PT6 Activity Against P2X Receptors

Peptides of the invention are investigated for the ability to modulate the activity of P2X receptors. Neurons for the experiments are isolated from dorsal root ganglia of 9-12-day Wistar rats. The ganglia are placed to a Petri dish filled with the extracellular solution (130 mM NaCl, 5 mM KCl, 2 mM $CaCl_2$, 2 mM $MgCl_2$, 20 mM HEPES, pH 7.4) at room temperature, and then transferred to the enzyme solution (1 mg of trypsin and 2 mg of collagenase in 2 ml of the extracellular solution) heated up to 35° C., and incubated for 10 min. Then the ganglia are rinsed thoroughly with a pure (without enzymes) extracellular solution in another Petri dish. Single cells are isolated from the rinsed ganglia using fine needles. A dish with single cells is transferred to the electrophysiological unit. The experiments begin after all cells are settled to the dish bottom in 30 min after isolation.

Electrophysiological tests are performed using the whole-cell configuration of the classic method of patch clamp and the approach of a rapid application of a substance (agonist), which binds to P2X3 receptors and induces ion channel opening. The electrophysiological setup consists of three parts: microscope; sample application system ("jumping table"; Pharma Robot, Ukraine); and recording system of the current flowing through channels in the cell plasma membrane. Isolated neurons in the Petri dish are placed under phase contrast microscope on the unit. Cells of 8-12 μm in diameter are selected for the experiment. A glass pipette electrode filled with the intracellular solution (120 mM CsF, 10 mM Tris-HCl, pH 7.2) is applied to each cell; as a result, a close contact is formed between the pipette and cell membrane with a resistance of the order of 1 Gohm. Then the cell on the pipette is brought up from the dish bottom and placed to the application tube. Solutions used in the experiment are placed in the chambers of the jumping table: solution 1, basic extracellular solution, in which the obtained cells are kept; solution 2, basic solution with addition of the agonist in the necessary concentration; solution 3, basic solution with peptide PT6 in the necessary concentration; solution 4, basic solution with the agonist and peptide PT6 in necessary concentration. The washout procedure is performed at least for 15 times within 3 min. The procedure is repeated 3 min after the agonist application. After recording control currents, peptide PT6 is applied to the cell. Then the procedure of cell treatment with PT6 is repeated. After agonist and PT6 application, cell washout from the agonist is performed in the presence of PT6. Successive agonist and PT6 application is stopped when the amplitude of P2X-mediated current remains unchanged. The ratio of control current amplitude and the established current amplitude at a given PT6 concentration is the value of efficacy for this PT6 concentration. Currents are recorded at the holding potential of −60 mV and room temperature with a Model 2400 Patch Clamp Amplifier (A-M Systems, USA). The electrodes for electrophysiological tests are made from borosilicate glass using a P-97 Flaming/Brown type micropipette puller (Sutter Instrument, USA), their resistance is 3-5 Mohm. As an agonist, cytidine triphosphate (CTP) in the saturating concentration (100 μM) is used. Current with a rapid rising phase (up to 12 msec) and rapid falling phase (up to 500 msec) corresponds to the current mediated by P2X3 receptors. The time of receptor activation is 2-4 msec; time of desensitization, 20-100 msec; and time of receptor exit from desensitization, about 2 min for CTP.

As a result of the experiment, it is suddenly discovered that binding of peptide PT6 to P2X3 receptors in the desensitized state leads to a significant decrease of the current amplitude. PT6 in concentration of 50 nM leads to the decrease of the current amplitude mediated by P2X3 receptors by 80% (FIG. 2). Therefore, peptide PT6 is a modulator, namely antagonist, of purinergic P2X3 receptors.

In the membranes of dorsal root ganglia, along with P2X3 receptors, P2X2 and P2X2/3 receptors are also found [Burgard E. C. et al. P2X receptor-mediated ionic currents in dorsal root ganglion neurons//J. Neurophysiol., 1999, V. 82, P. 1590-1598]. The time for exit of P2X3 receptors from desensitization is very large compared to P2X2 and P2X2/3 receptors. With the agonist application for 1 min, all observed responses, except for the first, are mediated by P2X2 and P2X2/3 receptors. The sensitivity of P2X2/3 receptor to ATP and α,β-methylene-ATP is similar (Kd ~30 μM), and the minimal concentration of α,β-methylene-ATP necessary for activation of P2X2 receptors is at least 100 μM. The equivalence of ionic currents observed in response to consecutive application of ATP and α,β-methylene-ATP indicates a significant predominance of P2X2/3 receptors on the cell membrane. In cells, which generate ionic currents of various amplitude, i.e. greater in response to ATP application, and very low in response to application of α,β-methylene-ATP, the membrane contains mainly P2X2 receptors. As a result of the experiment, it has been shown that PT6 does not affect ionic currents mediated by P2X2/3 and P2X2 receptors (FIG. 2). Therefore, it has been established suddenly that peptide PT6 acts selectively on the receptors of P2X3 isoform and is a selective antagonist of purinergic P2X3 receptors.

Despite the fact that the invention is described with reference to the disclosed variants of the implementation, it should be evident for specialists in the field that certain detailed experiments are presented only for the sake of illustration of the present invention, and they should not be considered in any way limiting the scope of the invention. It should be clear that various modifications are possible without divergence from the essence of the present invention.

The invention claimed is:

1. A peptide modulating the activity of purinergic P2X3 receptors with the following amino acid sequence:

(SEQ ID NO: 1)

$Gly^{1}$-$Tyr^{2}$-$Cys^{3}$-$Ala^{4}$-$Thr^{5}$-$Lys^{6}$-$Gly^{7}$-$Ile^{8}$-$Lys^{9}$-$Cys^{10}$-$Asn^{11}$-$Asp^{12}$-$Ile^{13}$-$His^{14}$-$Cys^{15}$-$Cys^{16}$-$Ser^{17}$-$Gly^{18}$-$Leu^{19}$-$Lys^{20}$-$Cys^{21}$-$Asp^{22}$-$Ser^{23}$-$Lys^{24}$-$Arg^{25}$-$Lys^{26}$-$Val^{27}$-$Cys^{28}$-$Val^{29}$-$Lys^{30}$-$Gly^{31}$.

2. A method of inhibiting purinergic P2X3 receptors in a subject in need thereof, the method comprising the step of administering to the subject a therapeutically effective amount of a peptide according to claim 1.

* * * * *